(12) United States Patent
Rayhanabad

(10) Patent No.: US 10,850,084 B1
(45) Date of Patent: Dec. 1, 2020

(54) ARTERIOVENOUS GRAFT AND METHOD OF PROVIDING DIALYSIS

(71) Applicant: Simon B. Rayhanabad, Huntington Beach, CA (US)

(72) Inventor: Simon B. Rayhanabad, Huntington Beach, CA (US)

(*) Notice: Subject to any disclaimer, the term of this patent is extended or adjusted under 35 U.S.C. 154(b) by 0 days.

(21) Appl. No.: 16/221,387

(22) Filed: Dec. 14, 2018

Related U.S. Application Data

(60) Provisional application No. 62/599,449, filed on Dec. 15, 2017.

(51) Int. Cl.
*A61M 39/02* (2006.01)
*A61M 1/36* (2006.01)
*A61M 25/00* (2006.01)
*A61M 1/14* (2006.01)

(52) U.S. Cl.
CPC .......... *A61M 39/0208* (2013.01); *A61M 1/14* (2013.01); *A61M 1/3655* (2013.01); *A61M 1/3661* (2014.02); *A61M 25/0032* (2013.01); *A61M 2025/006* (2013.01); *A61M 2039/0238* (2013.01)

(58) Field of Classification Search
CPC .......... A61M 39/0208; A61M 1/3661; A61M 25/0032; A61M 1/3655; A61M 1/14; A61M 2025/006; A61M 2039/0238
See application file for complete search history.

(56) References Cited

U.S. PATENT DOCUMENTS

| | | | | |
|---|---|---|---|---|
| 3,713,441 A * | 1/1973 | Thomas | ............. | A61F 2/06 604/8 |
| 3,818,511 A * | 6/1974 | Goldberg | ............. | A61M 1/3655 623/1.31 |
| 5,849,036 A * | 12/1998 | Zarate | ............. | A61F 2/06 623/1.31 |
| 6,146,414 A * | 11/2000 | Gelman | ............. | A61F 2/04 623/1.23 |
| 6,416,537 B1 * | 7/2002 | Martakos | ............. | A61F 2/06 623/1.13 |
| 8,313,524 B2 * | 11/2012 | Edwin | ............. | A61F 2/06 623/1.44 |
| 2010/0056978 A1 * | 3/2010 | Machan | ............. | A61M 1/3655 604/9 |

(Continued)

FOREIGN PATENT DOCUMENTS

WO    WO2016111642    7/2016

OTHER PUBLICATIONS

Jennings et al., The Venous Window Needle Guide, a hemodialysis cannulation device for salvage of uncannulatable arteriovenous fistulas, Journal of vascular surgery, vol. 60, Issue 4, pp. 1024-1032, Oct. 2014.

*Primary Examiner* — Leslie R Deak
(74) *Attorney, Agent, or Firm* — Steven R. Vosen

(57) ABSTRACT

An arteriovenous (AV) graft is disclosed than includes portions for inserting hemodialysis needles. The AV graft includes two spaced portions that are each adapted for receiving needles. These portions may have a different shape or rigidity than other portions of the AV graft. A care giver may be able to palpate the location of the two spaced portions, thus facilitating hemodialysis by providing the needles to locations on the AV graft adapted to accept the needles. Methods of providing hemodialysis using the AV graft are also described.

18 Claims, 5 Drawing Sheets

(56) References Cited

U.S. PATENT DOCUMENTS

2013/0274648 A1\* 10/2013 Weinberger ......... A61M 1/3655
                                                         604/9
2017/0304092 A1\* 10/2017 Hong ....................... A61F 2/06

\* cited by examiner

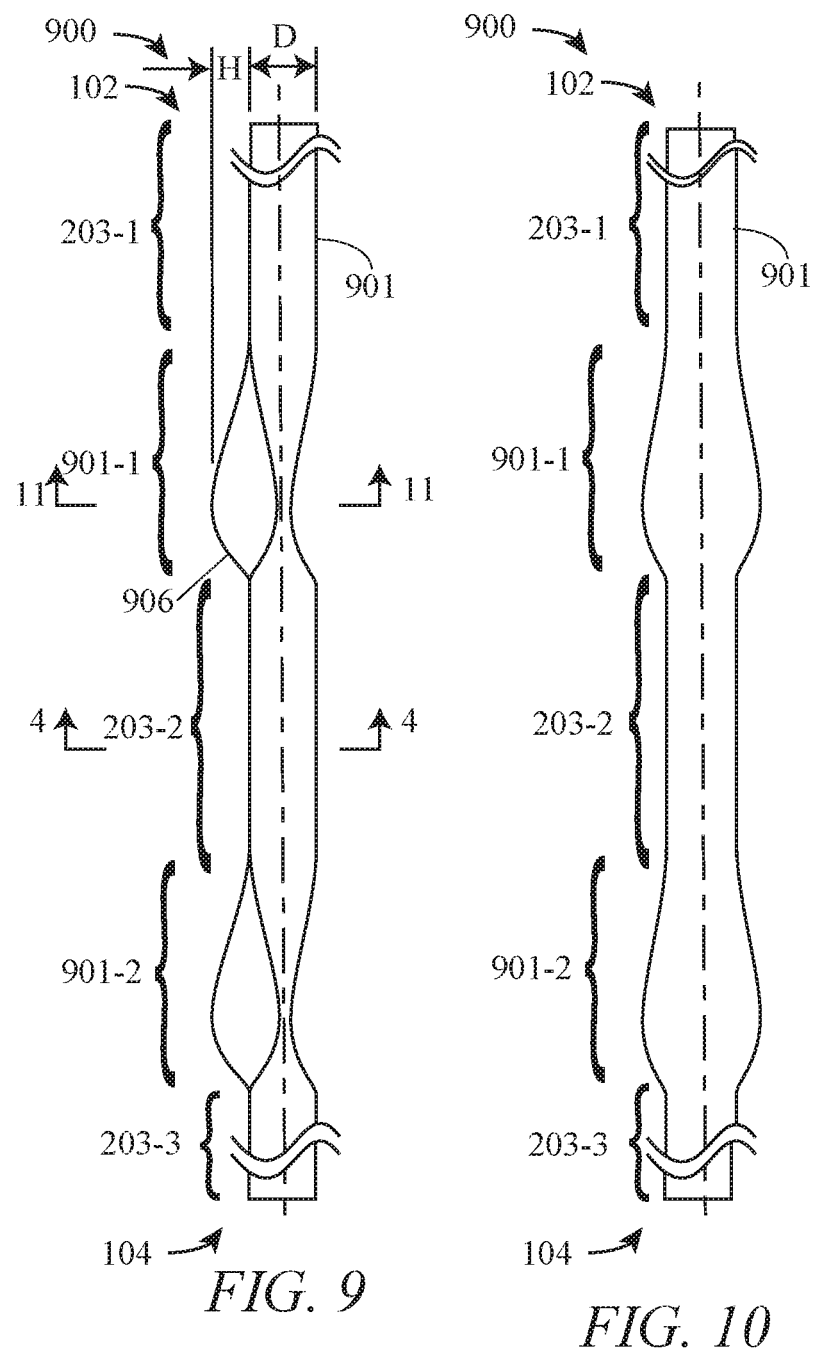
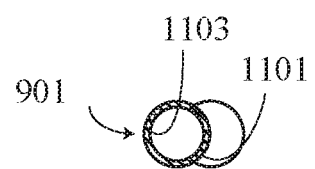
FIG. 11

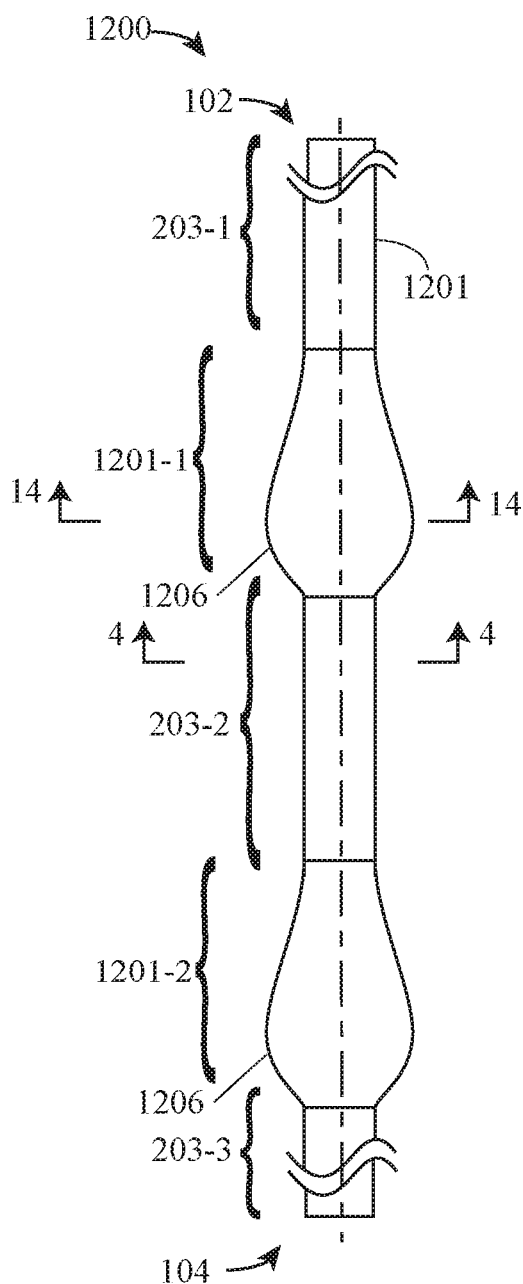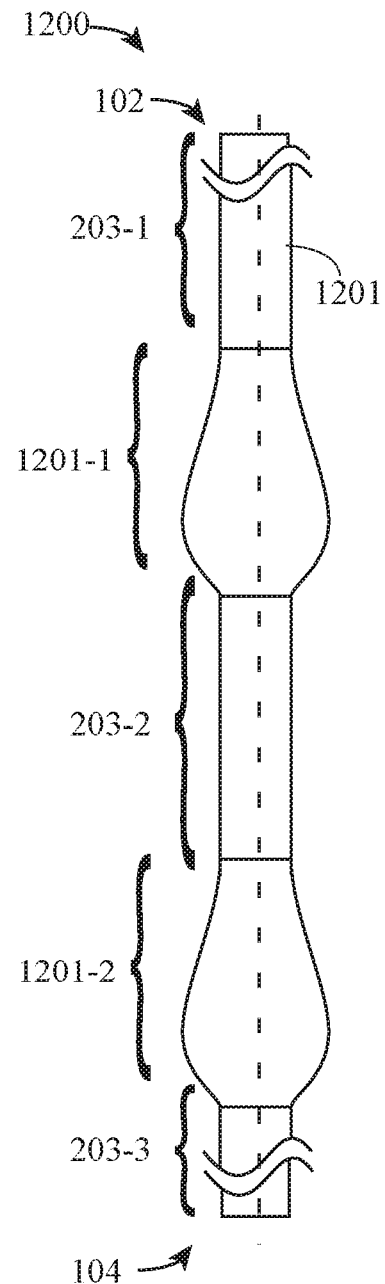
FIG. 12    FIG. 13
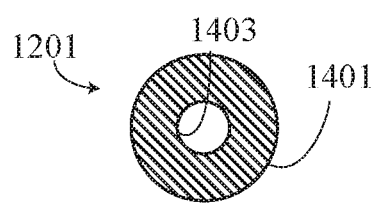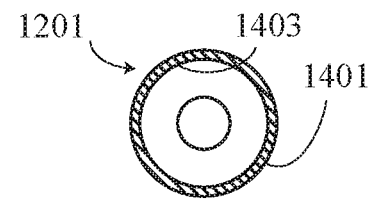
FIG. 14A    FIG. 14B

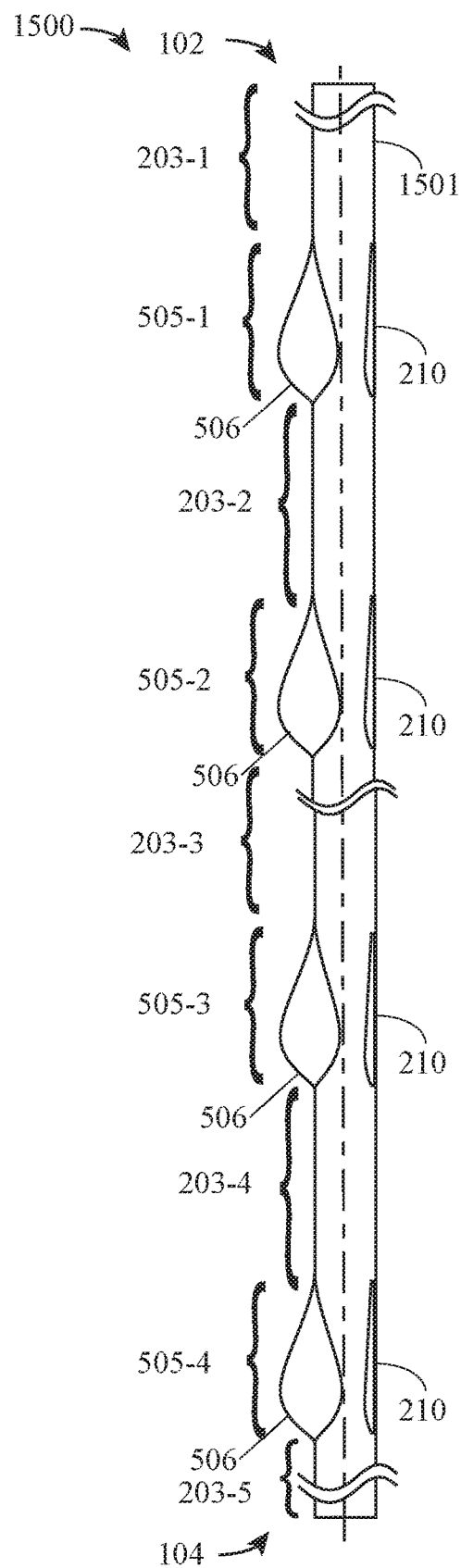
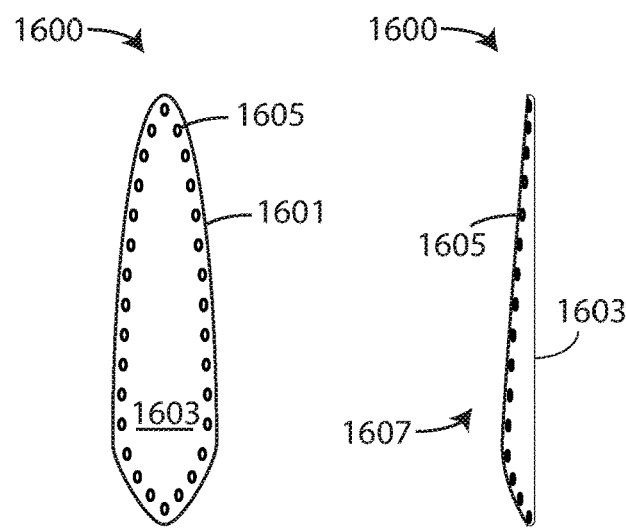
FIG. 16A    FIG. 16B
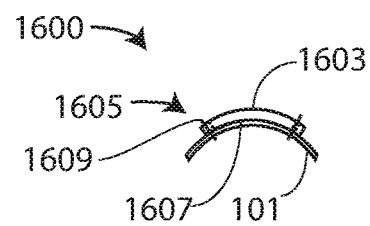
FIG. 16C
FIG. 15

ARTERIOVENOUS GRAFT AND METHOD OF PROVIDING DIALYSIS

CROSS-REFERENCE TO RELATED APPLICATIONS

This application claims the benefit of U.S. Provisional Application No. 62/599,449, filed Dec. 15, 2017, the contents of which are hereby incorporated by reference in its entirety.

BACKGROUND OF THE INVENTION

Field of the Invention

The present invention generally relates to dialysis, and more particularly to a method and system for surgically preparing a patient for dialysis.

Discussion of the Background

Background

In hemodialysis, an artificial kidney is used to remove waste and extra chemicals and fluid from a patient's blood. Typically, blood is removed from a first location in the patient's circulation system, is filtered, and is provided back into the patient at a second location that is downstream from the first location.

Vascular access to a patient may be obtained by inserting a pair of needles into the patient, where one needle is used to extract blood from the patient and deliver the blood to the artificial kidney, and the other needle is used to provide filtered blood from the artificial kidney back to the patient. A similar technique uses a single needle having a pair of lumens, where one lumen used to extract blood from the patient to the artificial kidney and the other lumen is used to provide filtered blood back to the patient.

In some cases, patients are prepared for hemodialysis by a minor surgical procedure to the arm or leg by implanting an arteriovenous (AV) graft under the skin. To undergo hemodialysis, needle(s) are inserted through the patient's skin and into the AV graft.

An example of a prior art AV graft 100 is illustrated in the front view of FIG. 1A and the sectional view of FIG. 1B.

AV graft 100 includes a tube 101 which may, for example and without limitation, have a lumen 103 with a diameter of from 5 mm to 24 mm, which extends between a pair of ends 102/104 with a length of from 10 cm to 80 cm, and may have wall thickness of from ¼ mm to ¾ mm. AV graft 100 is inserted into the patient with one end of the pair of ends 102/104 surgically attached to an artery and the other end of the pair of ends 102/104 surgically attached to a vein, such that blood flows from the artery to the vein through lumen 103. Tube 101 may be, for example and without limitation, be formed from a stretched polytetrafluoroethylene (PTFE), such as GORE-TEX® Vascular Graft (manufactured by W. L. Gore & Associates, Inc., Medical Products Division, Flagstaff, Ariz.). In some grafts may also include stiffening rings 105 attached to the outer surface of material 101 at regular intervals.

The nature of hemodialysis requires vascular access that is suitable for repeated puncture and allows a high blood flow rate for high-efficiency dialysis with minimal complications. One of the problems with prior art AV grafts is that it may be difficult to locate the graft so that is punctured property. Thus, for example, the graft may be difficult to accurately locate beneath the skin, or may move laterally when puncturing is attempted. Another problem with AV grafts is that, depending on the blood pressure, they may not necessarily hold their shape, and thus be difficult to puncture.

There is a need in the art for an AV graft that is easier to locate under the skin and which make is easier to find and puncture the graft with a needle for dialysis.

BRIEF SUMMARY OF THE INVENTION

The present invention overcomes the disadvantages of prior art by providing an AV graft that has a non-cylindrical shape. Several embodiments provide an AV graft having one or more bulges along its length. The bulges assist in locating the AV graft under the skin. In addition, if the bulge is formed from a thicker material than the other portions of the AV graft, the bulge will be even easier to locate and its thickness will allow it to more easily survive being punctured by a needle.

One aspect provides an arteriovenous graft including a lumen having a centerline that extends from a first arteriovenous graft end and a second arteriovenous graft end. The arteriovenous graft includes: a first lumen portion, a second lumen portion, and a third lumen portion disposed between said first lumen portion and said second lumen portion, where said first lumen portions and said second lumen portion both have a cross-sectional shape that is different from the cross-sectional shape of the third lumen portion relative to the centerline.

Another aspect provides an arteriovenous graft comprising: a first lumen portion, a second lumen portion, and a third lumen portion disposed between said first lumen portion and said second lumen portion, where said first lumen portion and said second lumen portion are more rigid than the third lumen portion.

Yet another aspect provides a method of proving hemodialysis using an arteriovenous graft of, comprising: providing the arteriovenous graft below the surface of the skin of a patient, where said providing includes attaching said first arteriovenous graft end to an artery and attaching said second arteriovenous graft end to a vein; and inserting a first hemodialysis needle through the skin of the patient and into said first lumen portion.

These features together with the various ancillary provisions and features which will become apparent to those skilled in the art from the following detailed description, are attained by the AV graft of the present invention, preferred embodiments thereof being shown with reference to the accompanying drawings, by way of example only, wherein:

BRIEF DESCRIPTION OF THE SEVERAL VIEWS OF THE DRAWING

FIG. 9 is a front view of a third embodiment AV graft;

FIG. 10 is a side view of the AV graft of FIG. 9;

FIG. 11 is a sectional view 5-5 of of FIG. 9;

FIG. 12 is a front view of a fourth embodiment AV graft;

FIG. 13 is a side view of the AV graft of FIG. 12;

FIG. 14A is a first embodiment sectional view 14-14 of FIG. 12;

FIG. 14B is a second embodiment sectional view 14-14 of FIG. 12; and

FIG. 15 is a side view of a fifth embodiment AV graft

FIG. 16A is a top view of one embodiment of a reinforcement;

FIG. 16B is a side view of the reinforcement of FIG. 16A; and

FIG. 16C is an end view of the reinforcement of FIG. 16A.

Reference symbols are used in the Figures to indicate certain components, aspects or features shown therein, with reference symbols common to more than one Figure indicating like components, aspects or features shown therein.

DETAILED DESCRIPTION OF THE INVENTION

Figure 1A:
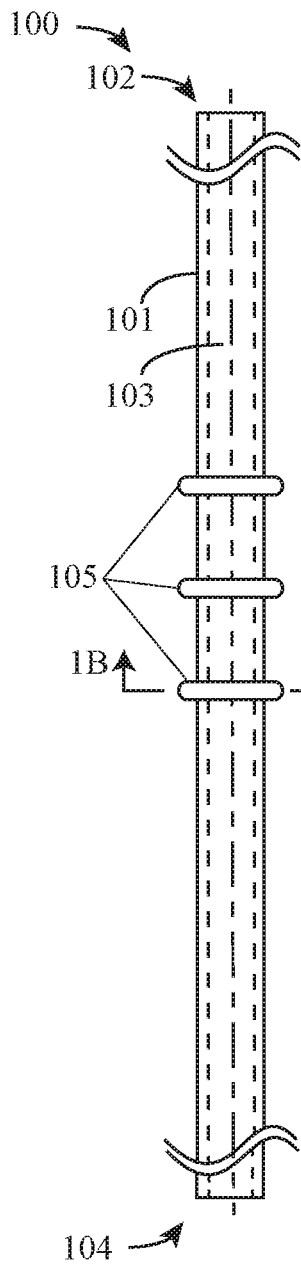
FIG. 1A is a front view of a prior art AV graft.
Figure 2:
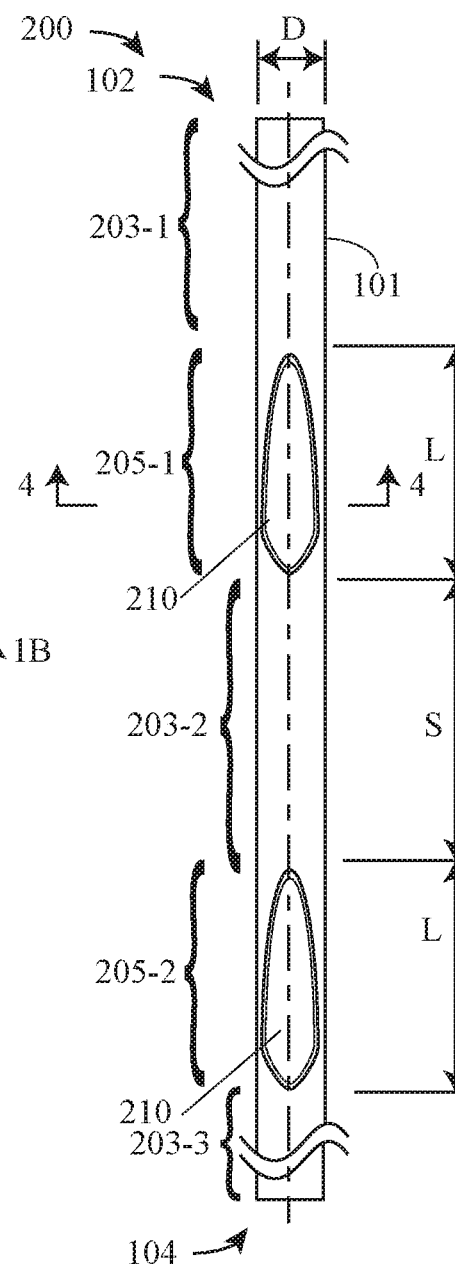
FIG. 2 is a front view of a first embodiment AV graft.
Figure 3:
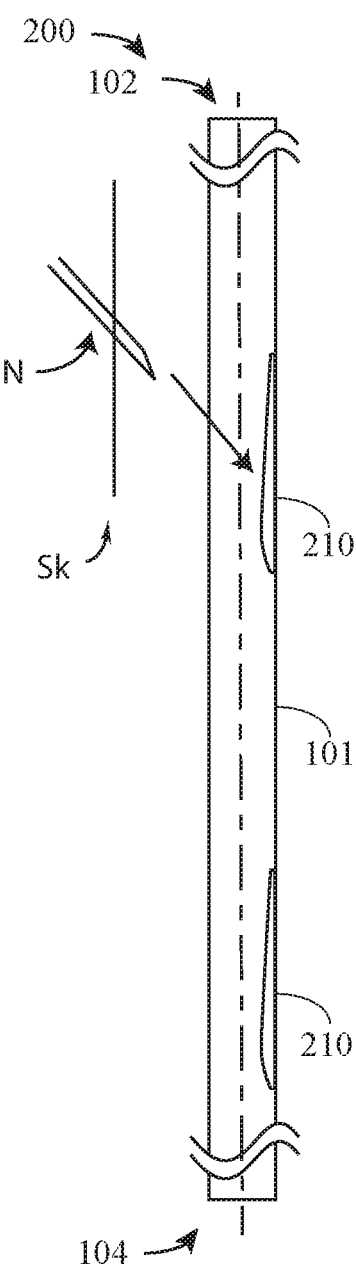
FIG. 3 is a side view of the AV graft of FIG. 2.
Figure 1B:
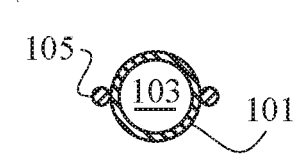
FIG. 1B is a sectional view 1B-1B of the prior art AV graft of FIG. 1A.
Figure 4:
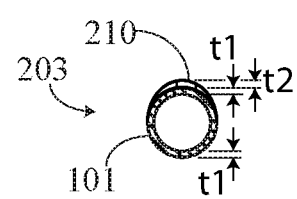
FIG. 4 is a sectional view 4-4 of FIG. 2.

FIGS. 2 and 3 are a front and side view, respectively, of a first embodiment AV graft 200, and FIG. 4 is a sectional view 4-4 of FIG. 2. AV graft 200 includes tube 101 that extends from first end 102 to second end 104 and includes several portions, including several portions 203 having a length S and indicated as portions 203-1, 203-2, and 203-3, and reinforced portions 205 having a length L and indicated as portions 205-1 and 205-2. The length L may be, for example and without limitation, 4 cm to 5 cm, and the length S may be, for example and without limitation, 4 cm to 5 cm. the lumen of tube 101 may be, for example, from 5 mm to 24 mm.

In certain embodiments, portions 203 are formed from tube 101, and portions 205 include tube 101 and an added reinforcement 210. Reinforcement 210 may be formed of the same material as tube 101 with a thickness resulting in portions 205 being more rigid than portion 203. Thus, for example, FIG. 4 shows tube 101 has a thickness t1, as described above, and that reinforcement 210 has a thickness t2, which may be for example and without limitation, approximately 0.50 mm, or may be 0.25 mm, 0.50 mm, 0.75 mm, or 1.00 mm.

In certain embodiments, reinforcements 210 are formed integral the formation of material 101, and in other embodiments, reinforcements 210 are formed separately from tube 101 and are affixed to tube 101, such as with an adhesive or by suturing reinforcements 210 to tube 101. In various embodiments, reinforcements 210 are formed from a biocompatible material, such as polytetrafluoroethylene (PTFE), formed into a fabric, such as Gore-Tex (W. L. Gore and Associates, Newark, Del.), or a metal such as stainless steel or titanium. Examples of embodiments of reinforcements 210 are discussed below and in co-owned U.S. patent application Ser. No. 16/186,555, filed Nov. 11, 2018, and which is hereby incorporated by reference in its entirely.

FIG. 3 illustrates the use of AV graft 200 for hemodialysis. AV graft 200 is surgically placed below the skin, Sk, of a patient with one of ends 102/104 attached to an artery and the other one of ends 102/104 attached to a vein, and with reinforcements 210 posterior to the skin. Each catheter of the pair of catheters, N, of a hemodialysis machine may then then inserted through the patient's skin, Sk, and into an anterior portion of AV graft 200, as illustrated by the arrow near needle N. The rigidity of reinforcement 210 prevents the need from passing through the posterior side of AV graft 200. The rigidity of reinforcement 210 also allows the care-giver to locate the reinforcements by palpation.

Figure 5:
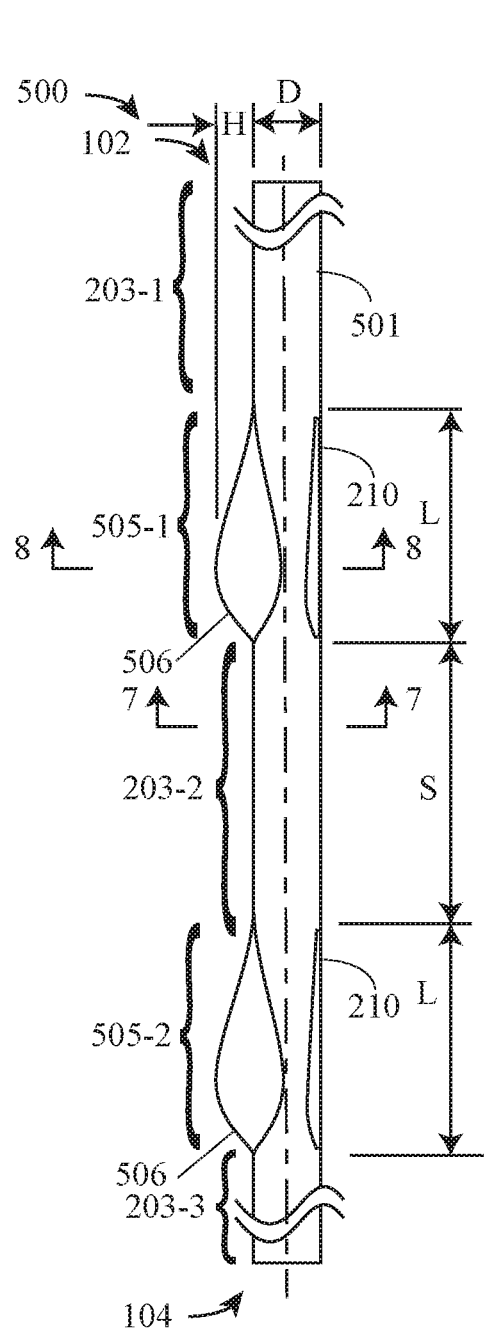
FIG. 5 is a front view of a second embodiment AV graft.
Figure 6:
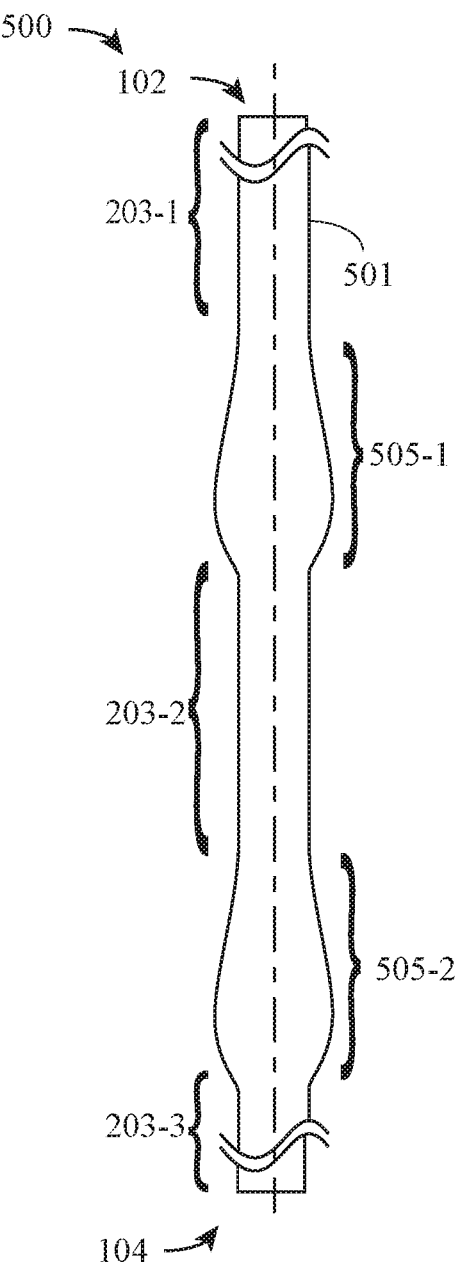
FIG. 6 is a side view of the AV graft of FIG. 5.

FIGS. 5 and 6 are a front and side view, respectively, of a second embodiment AV graft 500. AV graft 500 is generally similar to AV graft 200, except as explicitly stated.

AV graft 500 has an outer surface include both cylindrical and bulged portions. Thus, for example and without limitation, AV graft 500 is shown as including a tube 501 having a lumen that extends from first end 102 to second end 104. Tube 501 has several several portions along the length of the tube, such as several cylindrical portions 203 as discussed above, and indicated as 203-1, 203-2, and 203-3, and pair of bulged portions 505 (indicated as 505-1 and 505-2) each including a bulge 506. In general, some or all of the material of AV graft is flexible, and it to be understood that terms "bulged" and "cylindrical" refer to the shape when the AV graft is provided with a slight pressure, and that the actual shape may be deformed from what is illustrated. It is thus seen that the cross-sectional shape of tube 501 varies along the length of the tube.

Figure 7:
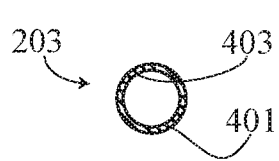
FIG. 7 is a sectional view 7-7 of FIG. 5.

FIG. 7 is a sectional view 7-7 of FIG. 5 and illustrates that, portions 203 are cylindrical and may have the same internal diameter as AV graft 200, such as D=5 mm to 24 mm, with a cylindrical outer wall 701 and a cylindrical inner wall 703.

Portions 505-1 and 505-2 may have the same general shape, and each extending a length L along AV graft 500, spaced by a cylindrical portion 203-2 having a length S. The length L may be, for example and without limitation, 4 cm to 5 cm, and the spacing S may be, for example and without limitation, 4 cm to 5 cm. Each portion has a bulge 506 that extends a distance H above the outer wall of portion 203, as illustrated in FIG. 5. In one embodiment, H is approximately equal to one half of the diameter D.

Figure 8A:
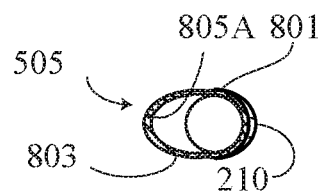
FIG. 8A is a first embodiment sectional view 8-8 of FIG. 5.

FIG. 8A is a first embodiment sectional view 8-8 of FIG. 5, illustrating portions 505 as having a thickness of wall 805A that is constant, resulting in a change in the shape of the lumen.

Figure 8B:
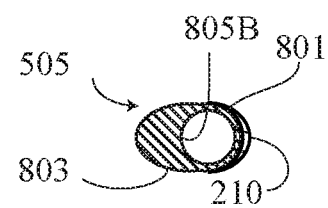
FIG. 8B is a second embodiment sectional view 8-8 of FIG. 5.

FIG. 8B is a second embodiment sectional view 8-8 of FIG. 5, illustrating that portions 505 as having a variable thickness of wall 805A such that the size of the lumen is constant along the length of AV graft 500

FIGS. 5, 8A and 8B show optional reinforcements 210 that are posterior to the bulge 506.

For use in hemodialysis, AV graft 500 is surgically placed below the skin of a patient with one end of the AV graft attached to an artery and the other end attached to a vein. Each catheter of the pair of catheters of a hemodialysis machine may then then inserted through the patient's skin and into the anterior part of AV graft 500, which is a bulge 506. The protruding shape of the bulged portion allows them to be easily located beneath the skin by palpation. The rigidity of optional reinforcement 210, which is posterior to the skin, prevents the need from passing through the posterior side of AV graft 500, and may also aid in locating the bulged portion under the skin.

FIGS. 9 and 10 are a front view and side view, respectively, of a third embodiment AV graft 900, and FIG. 11 is a sectional view 11-11 of FIG. 9. AV graft 900 is generally similar to AV grafts 200 or 500, except as explicitly stated.

AV graft 900 has an outer surface include both cylindrical and bulged portions. Thus, for example and without limitation, AV graft 900 is shown as including a tube 901 having a lumen that extends from first end 102 to second end 104. Tube 901 includes a pair of bulged portion 901-1/901-2 each having a bulge 906, and cylindrical portions 203 as discussed above. Thus, FIG. 11 shows portion 901 as including an outer diameter 1101 and an inner diameter 1103 of the lumen which are constant along the length of AV graft 900. AV graft 900 optionally includes reinforcements 210 (not shown) opposite each bulge, as in AV graft 200 or 500.

FIGS. 12 and 13 are a front and side view, respectively, of a fourth embodiment AV graft 1200. AV graft 1200 is generally similar to AV grafts 200, 500, or 900, except as explicitly stated.

AV graft 1200 has an outer surface include both cylindrical and bulged portions. Thus, for example and without limitation, AV graft 1200 is shown as including a tube 1201 having a lumen that extends from first end 102 to second end 104. AV graft 1200 includes a pair of cylindrically symmetrical bulged portion 1201-1/1201-2 each having symmetric bulge 1206 and cylindrical portions 203 as discussed above.

FIG. 14A is a first embodiment sectional view 14-14 of FIG. 12 and shows the outer surface 1401 and the lumen inner surface 1403. In this embodiment, the diameter the inner surface 1403 of the lumen is constant. FIG. 14B is a second embodiment sectional view 14-14. In this embodiment, the thickness of AV graft 1200 is constant along the length.

AV graft 100 optionally includes reinforcements 210 (not shown), as in AV grafts 200, 500, or 900.

FIG. 15 is a side view of a fifth embodiment AV graft 1500. AV graft 1500 is generally similar to any one of AV grafts 200, 500, 900, or 1200, except as explicitly stated.

AV graft 1500 has an outer surface include both cylindrical and bulged portions. Thus, for example and without limitation, AV graft 1500 is shown as including a tube 1501 having a lumen that extends from first end 102 to second end 104. Tube 1501 includes more than two bulged portions, illustrated as bulged portions 505, but which may alternatively be bulged portions 901 or 1201. Thus, for example and without limitation, FIG. 15 illustrates that AV graft 1500 includes 4 bulged portions 505-1, 505-2, 505-3, and 505-4, each with a bulge 506. AV graft 1500 thus allows for the selection of different bulged portions for inserting needles.

In certain other embodiments, an AV graft may have only one bulge portion or more than two bulge portions. In other embodiments, an AG graft has two bulge portions having different lengths, widths, heights, shapes, or hardness FIGS. 16A, 16B, and 16C are a top, side, and end view, respectively, of an alternative embodiment reinforcement 1600 which is generally similar to reinforcement 210, except as explicitly noted.

Reinforcement 1600 is formed from a material that is more rigid than the material of tube 101, and has an outer edge 1601, an outer surface 1603, and inner surface 1606, and a plurality of holes 1605 near the outer edge. As shown in FIG. 16C, reinforcement 1600 is placed with inner surface 1607 against tube 101, such as on the outside surface of AV graft 200, 500, 900, or 1200. Inner surface 1607 that is then affixed to material 102 using a thread 1609, which passes through tube 101 and holes 1605 around outer edge 1601, thus suturing reinforcement 1600 to tube 101.

In alternative embodiments, tube 101 and reinforcement 910 are affixed using an adhesive or other appropriate means of joining, in which case the reinforcement may or may not include holes 1605.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment. Furthermore, the particular features, structures or characteristics may be combined in any suitable manner, as would be apparent to one of ordinary skill in the art from this disclosure, in one or more embodiments.

Similarly, it should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

I claim:

1. An arteriovenous graft including a lumen that extends from a first arteriovenous graft end and a second arteriovenous graft end, said arteriovenous graft comprising:
   a first lumen portion,
   a second lumen portion,
   a third lumen portion disposed between said first lumen portion and said second lumen portion,
   a first end portion extending from the first lumen portion towards the first arteriovenous graft end, and
   a second end portion extending from the second lumen portion towards the second arteriovenous graft,
   where an outer surface of said third lumen portion, said first end portion, and said second portion each have a circumference equal to a first circumference,
   where an outer surface of said first lumen portion includes a first bulge portion which is asymmetric with respect to a first lumen portion longitudinal axis and has a circumference that varies smoothly along a longitudinal direction of the first lumen portion from said first circumference at ends of the first lumen portion to a maximum first bulge circumference between the ends of the first lumen portion that is greater than said first circumference,
   where an outer surface of said second lumen portion includes a second bulge portion which is asymmetric with respect to a second lumen portion longitudinal axis and has a circumference that varies smoothly along a longitudinal direction of the second lumen portion from said first circumference at ends of the second lumen portion to a maximum second bulge circumference between the ends of the first lumen portion that is greater than said first circumference, and
   where an inner diameter of said first lumen portion, an inner diameter of said second lumen portion, and an inner diameter of said third lumen portion are the same diameter.

2. The arteriovenous graft of claim 1, where said first lumen portion and said second lumen portion both have an outer surface that at least partially protrudes radially away from the arteriovenous graft further than the outer surface of said third lumen portion.

3. The arteriovenous graft of claim 1, where said first lumen portion includes a first reinforcement and said second lumen portion includes a second reinforcement, where said first reinforcement and said second reinforcement are not part of said third lumen portion, where said first reinforcement and said second reinforcement are both sufficiently strong to prevent a needle from puncturing the reinforcement.

4. The arteriovenous graft of claim 3, where said first reinforcement and said second reinforcement are more rigid than the third lumen portion.

5. The arteriovenous graft of claim 3, where said first reinforcement and said second reinforcement include a polytetrafluoroethylene (PTFE), a fabric, or a metal.

6. The arteriovenous graft of claim 5, where the metal is stainless steel or titanium.

7. The arteriovenous graft of claim 1, where the arteriovenous graft further comprises:
   a first reinforcement of the lumen material located on the first bulge portion proximal to the longitudinal axis of the first lumen portion; and
   a second reinforcement of the lumen material located on the second bulge portion proximal to the longitudinal axis of the first lumen portion.

8. The arteriovenous graft of claim 1, where said lumen includes a stretched polytetrafluoroethylene (PTFE).

9. A method of proving hemodialysis using an arteriovenous graft including a lumen that extends from a first arteriovenous graft end and a second arteriovenous graft end, said arteriovenous graft including a first lumen portion, a second lumen portion, a third lumen portion disposed between said first lumen portion and said second lumen portion, a first end portion extending from the first lumen portion towards the first arteriovenous graft end, and a second end portion extending from the second lumen portion towards the second arteriovenous graft, where an outer surface of said third lumen portion, said first end portion, and said second portion each have a circumference equal to a first circumference, where an outer surface of said first lumen portion includes a first bulge portion, where said first bulge portion is asymmetric with respect to a first lumen portion longitudinal axis and has a circumference that varies smoothly along a longitudinal direction of the first lumen portion from said first circumference at ends of the first lumen portion to a maximum first bulge circumference between the ends of the first lumen portion that is greater than said first circumference, where an outer surface of said second lumen portion includes a second bulge portion, where said second bulge portion is asymmetric with respect to a second lumen portion longitudinal axis having a circumference that varies smoothly along a longitudinal direction of the second lumen portion from said first circumference at ends of the second lumen portion to a maximum second bulge circumference between the ends of the first lumen portion that is greater than said first circumference, and where an inner diameter of said first lumen portion, an inner diameter of said second lumen portion, and an inner diameter of said third lumen portion are the same diameter, said method comprising:
   providing the arteriovenous graft below the surface of the skin of a patient, where said providing includes attaching said first arteriovenous graft end to an artery and attaching said second arteriovenous graft end to a vein; and
   inserting a first hemodialysis needle through the skin of the patient and into said first bulge portion.

10. An arteriovenous graft including a lumen that extends from a first arteriovenous graft end and a second arteriovenous graft end, said arteriovenous graft comprising:
   a tube having a diameter equal to a first diameter, where said tube includes
      a first lumen portion,
      a second lumen portion,
      a third lumen portion disposed between said first lumen portion and said second lumen portion,
      a first end portion extending from the first lumen portion towards the first arteriovenous graft end, and
      a second end portion extending from the second lumen portion towards the second arteriovenous graft,
   where an outer surface of said third lumen portion, said first end portion, and said second portion each have a circumference equal to a first circumference,
   where an outer surface of said first lumen portion includes a first bulge portion asymmetric with respect to a first lumen portion longitudinal axis, and includes a portion proximal to the longitudinal axis of the first lumen portion and a portion distal to the longitudinal axis of the first lumen portion,
   where an outer surface of said second lumen portion includes a second bulge portion asymmetric with respect to a second lumen portion longitudinal axis, and includes a portion proximal to the longitudinal axis of the second lumen portion and a portion distal to the longitudinal axis of the second lumen portion;
   a first reinforcement located on the first bulge portion proximal to the longitudinal axis of the first lumen portion, and
   a second reinforcement located on the second bulge portion proximal to the longitudinal axis of the second lumen portion,
   where said first reinforcement and said second reinforcement are both sufficiently strong to prevent a needle from puncturing the reinforcement.

11. The arteriovenous graft of claim 10, where said lumen includes a stretched polytetrafluoroethylene (PTFE).

12. The arteriovenous graft of claim 10, where said first reinforcement and said second reinforcement are more rigid than the third lumen portion.

13. The arteriovenous graft of claim 10, where said first reinforcement and said second reinforcement include a polytetrafluoroethylene (PTFE) a fabric or a metal.

14. The arteriovenous graft of claim 13, where the metal is stainless steel or titanium.

15. The arteriovenous graft of claim 10, where said first reinforcement and said second reinforcement are affixed to the first lumen portion and said second lumen portion, respectively.

16. The arteriovenous graft of claim 10, where said first reinforcement and said second reinforcement are integrated into said first lumen portion and said second lumen portion, respectively.

17. The arteriovenous graft of claim 10, where said first bulge portion has a circumference that varies smoothly along a longitudinal direction of the first lumen portion from said first circumference at ends of the first lumen portion to a maximum first bulge circumference between the ends of the first lumen portion that is greater than said first circumference.

18. The arteriovenous graft of claim 17, where said second bulge portion has a circumference that varies smoothly along a longitudinal direction of the second lumen portion from said first circumference at ends of the second lumen portion to a maximum second bulge circumference between the ends of the first lumen portion that is greater than said first circumference.

* * * * *